US007967807B2

(12) United States Patent
Murray

(10) Patent No.: US 7,967,807 B2
(45) Date of Patent: Jun. 28, 2011

(54) VASCULAR FLUOROSCOPIC MARKER

(75) Inventor: Robert Murray, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 589 days.

(21) Appl. No.: 11/687,026

(22) Filed: Mar. 16, 2007

(65) Prior Publication Data

US 2008/0228170 A1    Sep. 18, 2008

(51) Int. Cl.
*A61M 25/098* (2006.01)
(52) U.S. Cl. .......... 604/529; 623/1.34; 604/103.1; 604/362
(58) Field of Classification Search .......... 604/19, 604/529
See application file for complete search history.

(56) References Cited

U.S. PATENT DOCUMENTS

| 5,405,402 A | * | 4/1995 | Dye et al. ............. 623/22.38 |
| 5,421,832 A | | 6/1995 | Lefebvre |
| 5,556,413 A | | 9/1996 | Lam |
| 5,693,088 A | | 12/1997 | Lazarus |
| 2004/0093063 A1 | | 5/2004 | Wright et al. |

FOREIGN PATENT DOCUMENTS

| EP | 0592726 | 4/1994 |
| WO | WO98/09584 | 3/1998 |

* cited by examiner

*Primary Examiner* — Nicholas D Lucchesi
*Assistant Examiner* — Pritesh Patel

(57) ABSTRACT

A radiopaque marker configured for being securing to a tubular member adapted for introduction into a patient and having relief sections to provide localized accommodation of diametrical-circumferential dimensional reduction.

9 Claims, 4 Drawing Sheets

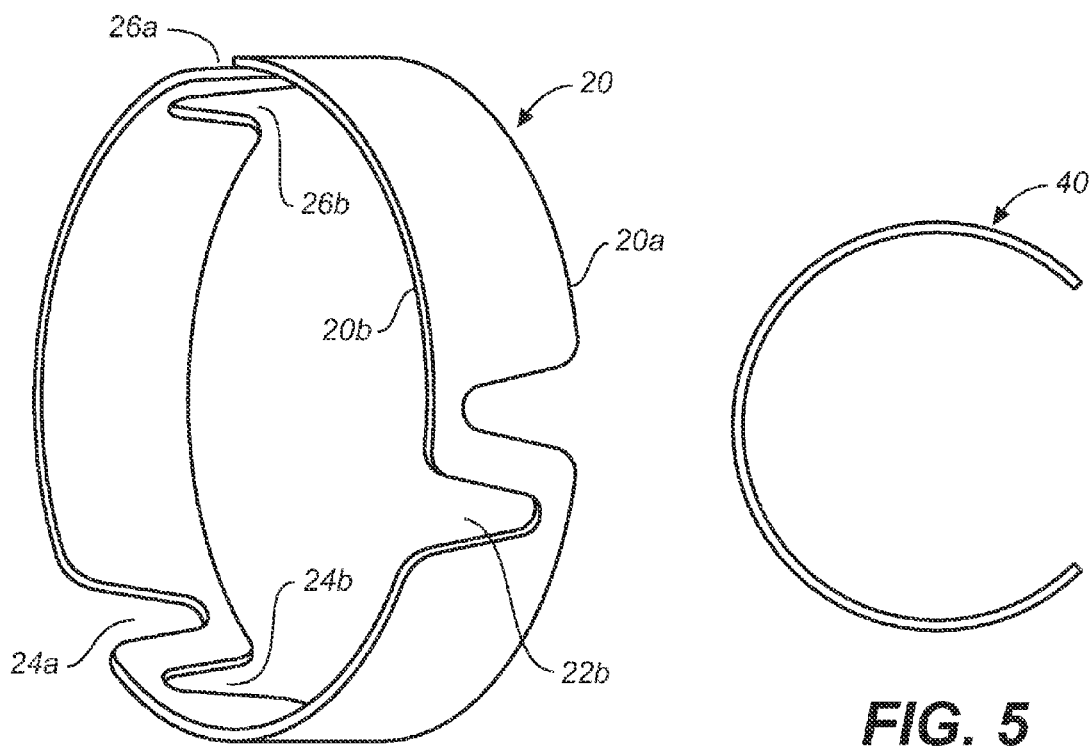
FIG. 1
FIG. 5
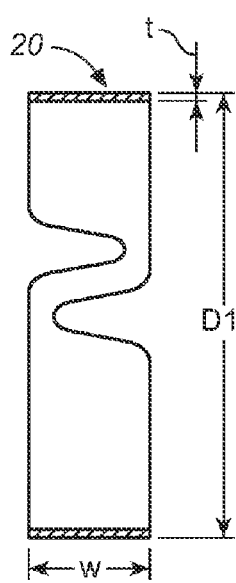 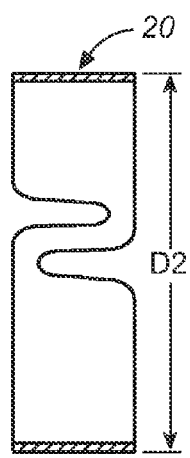 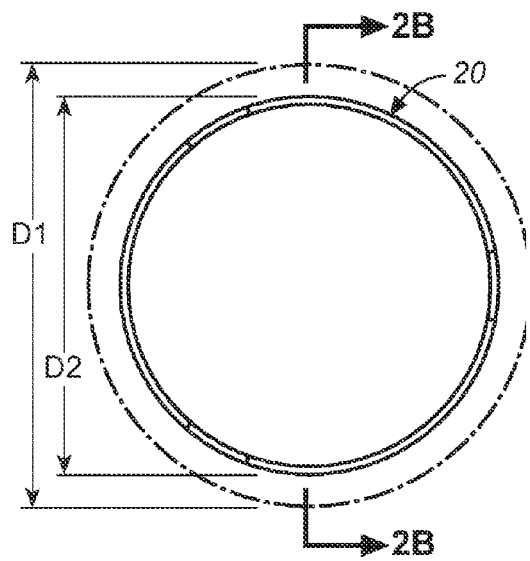
FIG. 2A  FIG. 2B  FIG. 2C

US 7,967,807 B2

VASCULAR FLUOROSCOPIC MARKER

FIELD OF THE INVENTION

The invention relates to several specific configurations of a radiopaque marker that can be applied to a tubular member for assisting in visualizing the position of the tubular member in a patient.

BACKGROUND OF THE INVENTION

Fluoroscopic markers (markers which are clearly identifiable under fluoroscopy) have been used on tubular devices for various medical procedures to facilitate imaging and/or tracking a portion of the tubular member in a patient. This can assist a physician with delivery of the tubular device, which can be a catheter or the like.

For example, fluoroscopic markers have been used on catheters that are designed for delivering tubular prosthesis. Tubular prostheses such as stents, grafts, and stent-grafts (e.g., stents having an inner and/or outer covering comprising graft material and which may be referred to as covered stents) have been widely used in treating abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., Dacron® or expanded polytetrafluoroethylene (ePTFE)) supported by a framework (e.g., one or more stent or stent-like structures), to treat or isolate aneurysms. The framework provides mechanical support and the graft material or liner provides a blood barrier.

Aneurysms generally involve abnormal widening of a duct or canal such as a blood vessel and generally appear in the form of a sac formed by the abnormal dilation of the duct or vessel. The abnormally dilated vessel has a wall that typically is weakened and susceptible to rupture. Aneurysms can occur in blood vessels such as in the abdominal aorta where the aneurysm generally extends below (distal to) the renal arteries or toward the iliac arteries.

In treating an aneurysm with a stent-graft, the stent-graft typically is placed so that one end of the stent-graft is situated proximally or upstream of the diseased portion of the vessel and the other end of the stent-graft is situated distally or downstream of the diseased portion of the vessel. In this manner, the stent-graft extends through the aneurysmal sac and spans and seals the proximal and distal ends thereof to replace or bypass the weakened portion. The graft material typically forms a blood impervious lumen to facilitate endovascular exclusion of the aneurysm.

Such prostheses can be implanted in an open surgical procedure or with a minimally invasive endovascular approach. Minimally invasive endovascular stent-graft use is preferred by many physicians over traditional open surgery techniques where the diseased vessel is surgically opened, and a graft is sutured into position bypassing the aneurysm. The endovascular approach, which has been used to deliver stents, grafts, and stent grafts, generally involves cutting through the skin to access a lumen of the vasculature. Alternatively, lumenar or vascular access may be achieved percutaneously via successive dilation at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly to a portion where it spans across the aneurysm where it is deployed.

When using a balloon expandable stent-graft, balloon catheters generally are used to expand the stent-graft after it is positioned at the target site. When, however, a self-expanding stent-graft is used, the stent-graft generally is radially compressed or folded and loaded into the distal end of a sheath or delivery catheter and self expands upon retraction or removal of the sheath at the target site. More specifically, a delivery catheter having coaxial inner and outer tubes arranged for relative axial movement therebetween can be used and loaded with a compressed self-expanding stent-graft. The stent-graft is positioned within the distal end of the outer tube (sheath) and in front of a stop fixed to distal end of the inner tube.

Regarding proximal and distal positions referenced herein, the proximal end of a prosthesis (e.g., stent-graft) is the end closest to the heart (by way of blood flow) whereas the distal end is the end furthest away from the heart during deployment. In contrast, the distal end of a catheter is usually identified as the end that is farthest from the operator, while the proximal end of the catheter is the end nearest the operator.

Once the catheter is positioned for deployment of the stent-graft at the target site, the inner tube is held stationary and the outer tube (sheath) withdrawn so that the stent-graft is gradually exposed and expands. An exemplary stent-graft delivery system is described in U.S. Patent Application Publication No. 2004/0093063, which published on May 13, 2004 to Wright et al. and is entitled Controlled Deployment Delivery System, the disclosure of which is hereby incorporated herein in its entirety by reference.

Although the endovascular approach is much less invasive, and usually requires less recovery time and involves less risk of complication as compared to open surgery, one challenge of this approach is positioning the catheter at the desired site. Fluoroscopic markers have been secured to catheters and the like to allow imaging and/or tracking of the catheter in a patient.

Radiopaque metal bands of fixed size have been attached to catheters and the like to provide a radiopaque marker to assist in locating the position of the catheter using conventional fluoroscopic techniques. These bands typically are not compressed onto the tubular catheter to secure it to the catheter as the band can wrinkle or kink, which can result in an undesirable increase in profile. Where wrinkling (or the presence of a raised portion on) the marker means the presence of a localized discontinuity greater than 0.0015 inches in the radius (0.003 inches in the diameter) of the marker measurable at a high or low point on the marker between adjacent marker band radiuses of substantially equal radial dimension such that the wrinkle (raised portion) is created when the marker ring is compressed from a first larger nominal diameter to a second smaller nominal diameter. Therefore, these fixed diameter bands generally must provide a close fit with the catheter and may need to be glued, crimped or pressed to the catheter to avoid slippage during multi step lamination of the catheter tube as it is constructed with an embedded marker. Other approaches have included, cutting a polymer tube that has been doped with radiopaque material to form a band that can be secured to the catheter or the like. The tube can be made by melting a polymer and adding metal powder so that the volume of metal is about 50 to about 75% of the volume of the tube. After a band is cut from the tube and placed over the catheter, it is bonded to the catheter with a laminate using heat treatment as is known. Alternatively, the band can be butt welded to the catheter with heat as is known. However, one drawback associated with using such a metal powder based ring is that the metal powder can cause degradation of the native polymer of the band and adversely impact its strength as it ages. Further, since the band is not pure metal, typically a thicker band is required to provide the same radiopacity as a metal band and this increases the profile of the device.

Accordingly, there remains a need to develop and/or improve fluoroscopic markers.

SUMMARY OF THE INVENTION

The present invention involves improvements in radiopaque marker construction.

In one embodiment according to the invention, a method of securing a radiopaque marker to a tubular member adapted for introduction into a patient, comprises sliding a radiopaque marker ring over a tubular member adapted for introduction into a human patient; and reducing the diameter of the radiopaque marker ring without wrinkling the marker.

In another embodiment according to the invention, a radiopaque marker comprises a ring shaped member having at least a portion of which is in the form of a band having side edges, a region between the side edges, and at least two edges extending from the region to at least one of the side edges to form a gap in the band.

In another embodiment according to the invention, a radiopaque marker comprises a ring shaped member comprising radiopaque material having a least one cut-out section to absorb stress when the ring shaped member is radially compressed.

In another embodiment according to the invention, a tubular apparatus for introduction into a patient comprises a tubular member adapted for introduction into a lumen in a human patient; and a radiopaque marker surrounding a portion of the tubular member and having at least one circumferentially compressed cut-out section.

Other features, advantages, and embodiments according to the invention will be apparent to those skilled in the art from the following description and accompanying drawings.

BRIEF DESCRIPTION OF THE DRAWINGS

FIG. 1 illustrates one embodiment of a marker in accordance with the invention.

FIG. 2A is a sectional view of the marker of FIG. 1.

FIG. 2B is a sectional view of the marker of FIG. 1 in a radially compressed state.

FIG. 2C is a side view of the marker of FIG. 1 illustrating first and second diametrical dimensions before and after radial compression.

FIG. 4A depicts a piece of tubing, FIG. 4B depicts the end of the tubing with the desired cut-outs, and FIG. 4C depicts a cutting line in phantom to illustrate where the tubing is cut to form the markers second side edge.

FIG. 5 illustrates another embodiment according to the invention.

FIG. 6 illustrates securing the marker around the tubular member with a shrink wrap method and FIG. 7 illustrates the marker secured to the tubular member after shrink wrap.

DETAILED DESCRIPTION

Figure 3:
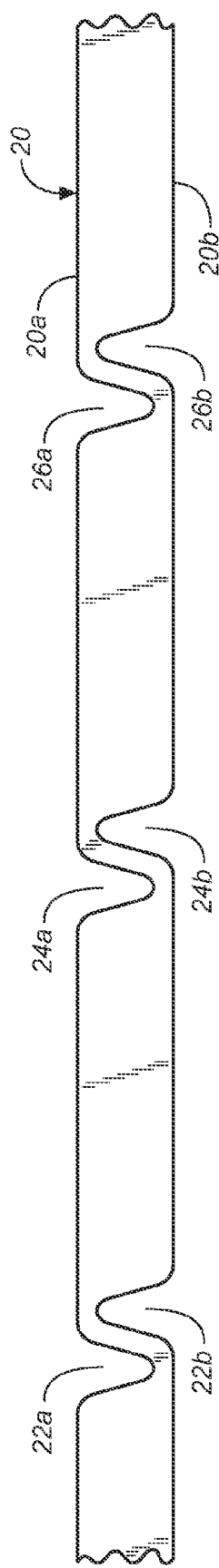
FIG. 3 depicts the marker of FIG. 1 opened and rolled out.

The following description will be made with reference to the drawings where when referring to the various figures, it should be understood that like numerals or characters indicate like elements.

According to various embodiments of the invention, a marker, which can be in the form of a band, is provided with a construction to facilitate its securement to a tube or lumen that is configured for introduction into a patient. The marker is constructed to allow its radial compression and/or diametrical reduction over a tube or lumen, while minimizing or eliminating the risk of it kinking or wrinkling. The marker can have relief sections for accommodating a reduction in its diameter or circumference. In one example, the marker can include one or more cut-outs to allow diametrical or circumferential reduction when subjected to radial compression. In the case where a plurality of cut-outs are used, they can be asymmetrically or symmetrically arranged.

The tube or lumen to which the marker is attached can be any tube or lumen that requires a radiopaque marker and can be, for example, a graft cover for delivery of a stent-graft, a sheath (e.g., an introducer sheath for a femoral artery), a guide catheter (e.g., a guide catheter for percutaneous devices, which can be adapted for coronary, peripheral or other applications), a guidewire lumen (e.g., a guidewire lumen for percutaneous translumenal angioplasty devices (PTAs) such as balloons or stent balloons), or other suitable tube or lumen.

Referring to FIG. 1, one embodiment of a marker according to the invention is shown and generally designated with reference numeral 20. In the illustrative example, marker 20 has a ring shaped band configuration with a plurality of cut-outs that are symmetrically arranged. There are three cut-out pairs 22a,b, 24a,b, and 26a,b which are approximately equidistantly spaced from one another. Each cut-out has a closed end and an open end and extends from a point between the opposed side edges 20a and 20b of the marker band to one of the edges where it opens. In the region of each cut-out pair (see e.g., FIGS. 2A and 3), the marker band has a configuration that resembles a sinusoidal shape and which defines the generally U-shaped cut-outs. Although three pairs of U-shaped cut-outs are shown, other arrangements, configurations or shapes can be used. The number of cut-out pairs can vary or the number of cut-outs in a group can vary as well as their position. For example, three groups of three cut-outs or four groups of two cut-outs (a cut-out pair) can be used. Further, a single cut-out can be used. The cut-out shape or configuration also can vary and can be V-shaped or any other suitable configuration.

Referring to FIGS. 2A and 2B, sectional views of the marker 20 in an uncompressed state (FIG. 2A) and a radially compressed state (FIG. 2B) are shown, where the width or angle of the cut-outs has been reduced and the diameter of the marker has been reduced from D1 to D2. The illustrated cut-out angle, which is defined by the edge face interconnecting the inner and outer circumferential surfaces of the ring, typically changes about 5-10° upon deformation of the cut-out defining sinusoidal section when compressed. FIG. 2C is a side view of the marker 20 illustrating the first and second diametrical dimensions of FIGS. 2A and 2B. FIG. 3 shows the marker 20 opened and rolled out to further illustrate the cut-outs and the sinusoidal sections of the band.

As shown in the example illustrated in FIGS. 2A-C, the marker circumference or diameter can be reduced without creating a localized bend in the material sufficient to cause a radially extending raised portion (e.g., a ridge) in the inner or outer surface of the marker ring.

Figure 4A:
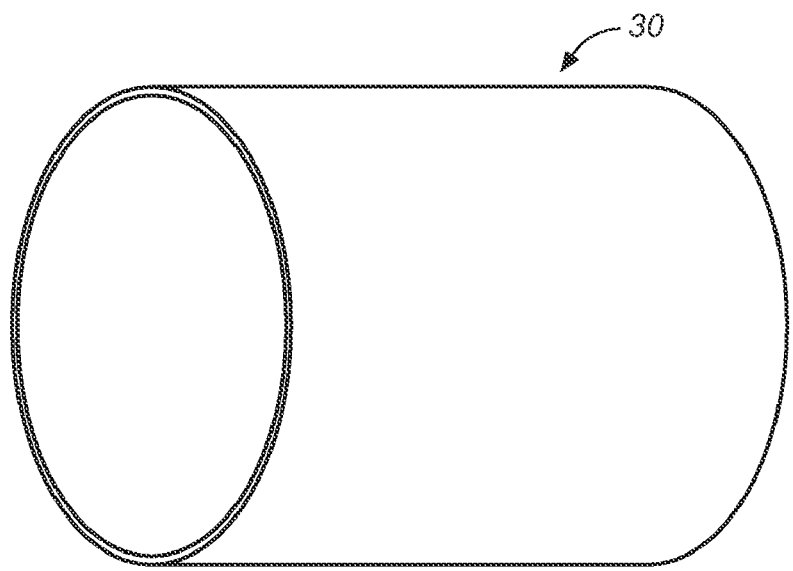
FIGS. 4A-C illustrate manufacture of the marker of FIG. 1, where
Figure 4B:
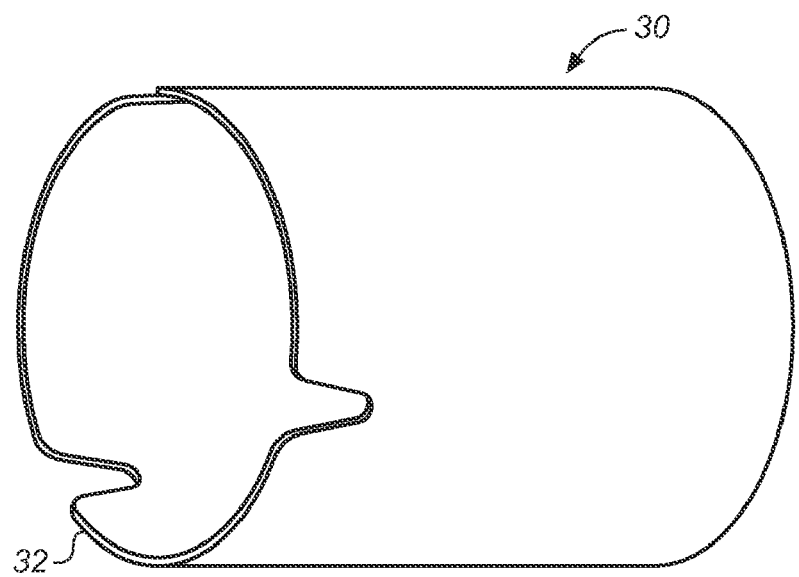
Figure 4C:
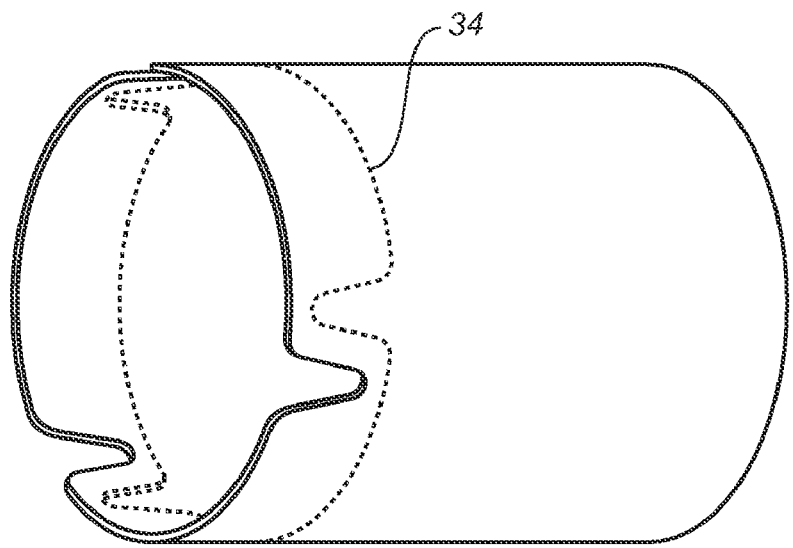

FIGS. 4A-C illustrate manufacture of the marker 20, where FIG. 4A depicts a piece of tubing 30, FIG. 4B depicts one end 32 of tubing 30 with the desired cut-outs, and FIG. 4C depicts a cutting line 34 in phantom, which is then cut to form a marker 20, while leaving another cut end of the tubing to form another band. Such cutting can be done by a laser or high pressure water jet, for example.

The marker can be made from platinum iridium (PtIr), tungsten, gold or any other suitable radiopaque material and can be selected so as to be semi-ductile depending on the application. Referring to FIG. 2A, the width "W" of the marker can be from about 1-5 mm, and typically is about 3 mm. The thickness "t" typically will range from about 0.005 to about 0.030 inch. The diameter "D1" typically will range from about 0.010 to about 0.250 inch depending on the application. For example, a 0.014 inch diameter can be used for a coronary guidewire lumen, a 0.020 inch diameter can be used for coronary stents or balloon angioplasty, and a 0.250 inch diameter can be used for a vascular graft such as an AAA graft for an abdominal aortic aneurysm.

FIG. 5 illustrates another embodiment of a marker according to the invention and is generally designated with reference numeral 40. In this embodiment, marker 40 has a C-shaped configuration and can be in the form of a band as is exemplary marker 20. When marker 40 is radially compressed, its ends move toward one another to reduce the marker's diameter and the gap between the ends, while minimizing or eliminating any wrinkle formation in the marker band. The dimensions and materials described in connection with marker 20 can be used.

Figure 6:
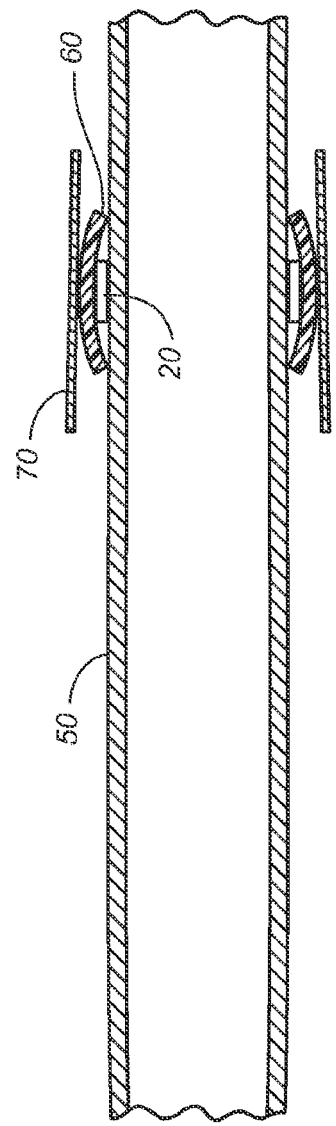
FIGS. 6 and 7 illustrate securing the marker of FIG. 1 to a tubular member where
Figure 7:
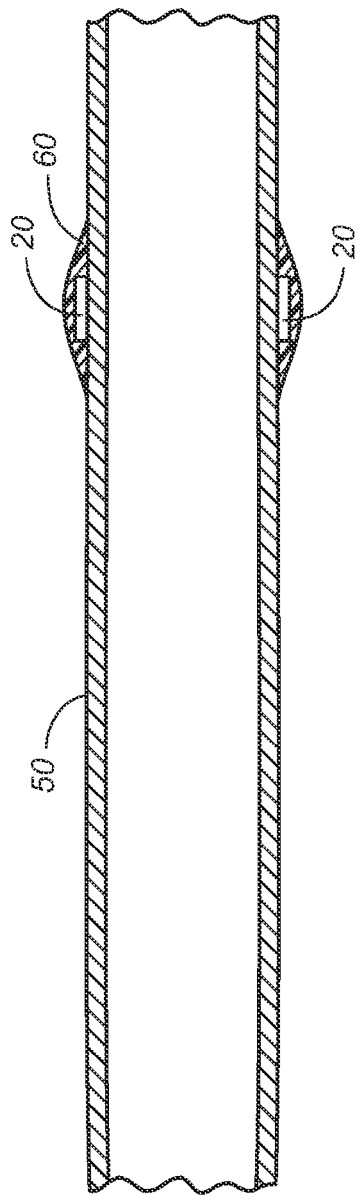

FIGS. 6 and 7 illustrate securing marker 20 to a tubular member or lumen. In use annular marker 20 is slid over tube 50 to a desired location, where the marker is radially compressed (e.g., using a radial compression tool having at least as many inwardly compressing elements or surfaces as the band has solid sections between cutout sections) to reduce its diameter and hold it in or secure it to the selected location. In this position, marker 20 has a central axis which is generally coaxial with the central axis of tube 50. In this example, it is further noted that the cut-outs in marker 20 extend in a direction generally parallel to the central axis of marker 20 and therefore they also extend generally parallel to the central axis of tube 50.

A laminate tube (e.g., laminate tube 60) is slid over tube 50 and marker 20 to cover marker 20. The laminate tube typically has a length of about three times the width of marker 20 and comprises any suitable material such as a polymeric material (e.g., nylon, PET, or Pebax). The laminate is selected to fuse with the material of tube 50 during a conventional shrink wrap procedure. A shrink wrap tube 70, which typically has a length of about twice that of the laminate tube, is then positioned over the laminate tube and heated so that it heats laminate tube 60 and shrinks, thereby compressing laminate tube 60 while tube 60 is heated. The shrink wrap tube is then removed. Typically the shrink wrap tube is heated to about 300-350° F. and is made from a material that is dissimilar to the laminate tube and in the illustrative embodiment can be, for example, polyester or polyethylene. It should be understood, however, that shrink wrap procedures are well known and any other suitable shrink wrap procedure can be used.

According to another method of attaching the marker to the tubular member, the marker is crimped so that it is embedded in the tubular member. This may require a thicker and relatively soft tubular member such as tubular member made of polyurethane, nylon or Pebax and having a wall thickness of about 0.010 inch or more. In this example, the laminate and laminate procedure need not be used.

Figure 8:
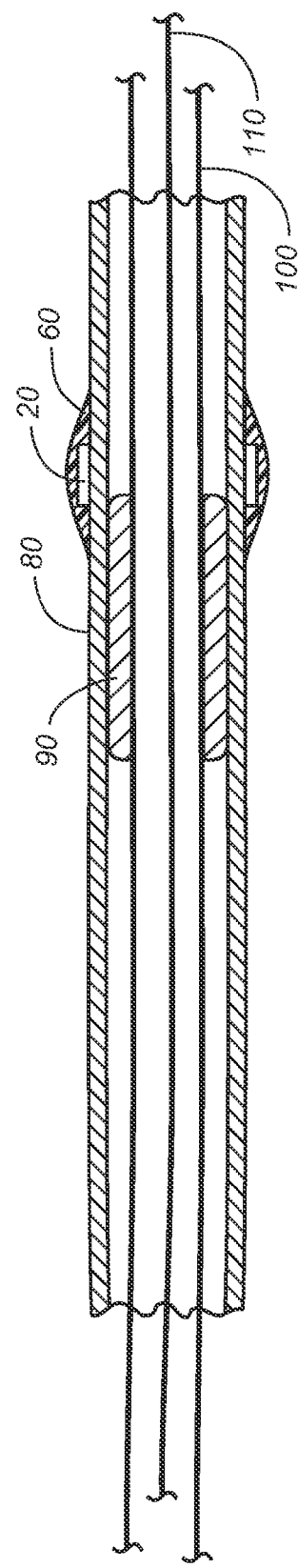
FIG. 8 illustrates another tubular member configuration having the marker of FIG. 1 secured thereto.

Referring to FIG. 8, another tubular member configuration is shown where the tubular member to which marker 20 is secured in accordance with the foregoing is a graft cover 80. Graft cover 80, which corresponds to one example case of generic tube 50, surrounds conventional, expandable stent-graft 90, which is in a radially collapsed state and which surrounds a portion of guide wire tube 100. Guide wire tube 100 is configured for tracking over guidewire 110 as is known in the art. Laminate 60 is applied to marker 20 and tube 80 as described above. Marker 20 can be secured to any suitable graft cover and delivery system.

One example of a stent-graft delivery system to which marker 20 can be attached comprises a catheter tube or graft cover 80 (outer tube) and inner guidewire tube 100, which are coaxial and arranged for relative axial movement therebetween. The prosthesis (e.g., stent-graft 90) is positioned within the distal end of outer tube 80 and in front of a pusher member or stop (not shown) as is known in the art and which is concentric with and secured to inner guidewire tube 100 and can have a disk or ring shaped configuration with a central access bore to provide access for guidewire tube 100. Once the catheter is positioned for deployment of the prosthesis at the desired site using marker 20, the inner member or guidewire lumen 100 with the stop are held stationary and the outer tube or graft cover 80 withdrawn so that graft cover 80 is displaced from a conventional tapered tip or obturator (not shown and to which the stent-graft is coupled in a conventional manner) and the stent-graft gradually exposed and allowed to expand. The stop therefore is sized to engage the distal end of the stent-graft as the stent-graft is deployed. The proximal ends of sheath 80 and inner tube or guidewire lumen 100 are coupled to and manipulated by a handle (not shown). The tapered tip or obturator optionally can include a stent-graft tip capture mechanism to receive and hold the proximal end of the stent-graft so that the operator can allow expansion of the stent-graft proximal end during the last phase of its deployment. In this regard, any of the stent-graft deployment systems described in U.S. Patent Application Publication No. 2004/0093063, referenced above can be used and marker 20 incorporated therein.

Any feature described in any one embodiment described herein can be combined with any other feature of any of the other embodiments whether preferred or not.

Variations and modifications of the devices and methods disclosed herein will be readily apparent to persons skilled in the art.

What is claimed is:

1. A radiopaque marker comprising:
a band having a longitudinal central axis and width between opposed side edges thereof,
said band having cut out sections and solid sections between said cut out sections,
wherein one cut out section of said cut out sections comprises at least a cut out pair of cut out openings and where one of said solid sections extends circumferentially from one of said cut out openings a distance substantially greater than the circumferential distance that the one of said cut out openings circumferentially extends,
wherein each cut out opening of said cut out openings extends from a closed end located within the band between the opposed side edges of the marker band to an open end at one of the edges where it opens, a portion of the band extends between the cut out openings to connect the solid sections on each side of the cut out section.

2. The radiopaque marker of claim 1 wherein cut out openings of said cutout section in said marker band extend in a direction generally parallel to said longitudinal central axis of the marker band.

3. The radiopaque marker of claim 1, wherein said marker band between said solid sections has a configuration that resembles a sinusoidal shape.

4. The radiopaque marker of claim 3, wherein each cut out opening has a U-shaped configuration.

5. The radiopaque marker of claim 1 wherein the number of cut out sections ranges from 3 to 4 inclusive.

6. The radiopaque marker of claim 5 wherein one cut out section includes three cut out openings.

7. The radiopaque marker of claim 1, wherein said cutout sections are approximately equidistantly spaced from each other.

8. The radiopaque marker of claim 1 wherein said marker band cut out openings between said solid sections form a cut-out angle, which is defined by an edge face interconnecting the inner and outer circumferential surfaces of the ring, this cut out angle typically changes about 5-10° upon deformation of the cut out section when compressed.

9. The marker of claim 1, wherein said band has between one and four cut out sections, wherein the number of cut out sections can vary or the number of cut out openings in cut out section can vary as well as their position, such there may be three cut out sections of three cut out openings or four cut out sections of two cut out openings.

* * * * *